(12) United States Patent
Wildman et al.

(10) Patent No.: US 7,907,053 B2
(45) Date of Patent: Mar. 15, 2011

(54) COMBINED LOCATING, TRACKING AND COMMUNICATIONS SYSTEM

(75) Inventors: Timothy D. Wildman, Metamora, IN (US); William F. Collins, Jr., Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1198 days.

(21) Appl. No.: 10/556,670

(22) PCT Filed: May 14, 2004

(86) PCT No.: PCT/US2004/015107
§ 371 (c)(1),
(2), (4) Date: Oct. 3, 2006

(87) PCT Pub. No.: WO2004/104619
PCT Pub. Date: Dec. 2, 2004

(65) Prior Publication Data
US 2007/0106518 A1    May 10, 2007

Related U.S. Application Data

(60) Provisional application No. 60/470,406, filed on May 14, 2003.

(51) Int. Cl.
*G08B 13/14* (2006.01)
(52) U.S. Cl. ............... 340/572.1; 340/539.1; 340/539.13
(58) Field of Classification Search .... 340/572.1–572.8, 340/539.1, 539.13
See application file for complete search history.

(56) References Cited

U.S. PATENT DOCUMENTS

| | | | |
|---|---|---|---|
| 4,275,385 | A | 6/1981 | White |
| 4,601,064 | A | 7/1986 | Shipley |
| 5,119,104 | A * | 6/1992 | Heller ........................ 342/450 |
| 5,291,399 | A | 3/1994 | Chaco |
| 5,387,993 | A | 2/1995 | Heller et al. |
| RE35,035 | E | 9/1995 | Shipley |
| 5,455,851 | A | 10/1995 | Chaco et al. |
| 5,465,082 | A | 11/1995 | Chaco |
| 5,515,426 | A | 5/1996 | Yacenda et al. |
| 5,548,637 | A | 8/1996 | Heller et al. |

(Continued)

FOREIGN PATENT DOCUMENTS

WO    WO 02/091297    11/2002

OTHER PUBLICATIONS

Wong, C. et al. Hybrid Tracking Technology, Security Technology, Proceedings, Institute of Electrical and Electronics Engineers 1993, International Carnahan Conference on Ottawa, ONT. Canada Oct. 1993, pp. 195-200.

*Primary Examiner* — Eric M Blount
(74) *Attorney, Agent, or Firm* — Barnes & Thornburg LLP

(57) ABSTRACT

A combined locating, tracking and communications system (10), including a server (12), a plurality of area transceivers (14) configured to communicate with the server (12) and having an associated reception range (34), a plurality of zone transceivers (16) configured to communicate with the area transceiver (14), a plurality of tags (18) configured to communicate with the area transceiver (14) and the plurality of zone transceivers (16), and a plurality of portable communicators (20) configured to communicate with the area transceiver (14) and the plurality of zone transceivers (16).

22 Claims, 3 Drawing Sheets

U.S. PATENT DOCUMENTS

| | | | |
|---|---|---|---|
| 5,561,412 A | 10/1996 | Novak et al. | |
| 5,572,195 A | 11/1996 | Heller et al. | |
| 5,594,786 A | 1/1997 | Chaco et al. | |
| 5,633,742 A | 5/1997 | Shipley | |
| 5,689,229 A | 11/1997 | Chaco et al. | |
| 5,699,038 A | 12/1997 | Ulrich et al. | |
| 5,745,272 A | 4/1998 | Shipley | |
| 5,818,617 A | 10/1998 | Shipley | |
| 5,822,418 A | 10/1998 | Yacenda et al. | |
| 5,822,544 A | 10/1998 | Chaco et al. | |
| 5,838,223 A | 11/1998 | Gallant et al. | |
| 6,344,794 B1 | 2/2002 | Ulrich et al. | |
| 6,462,656 B2 | 10/2002 | Ulrich et al. | |
| 6,727,818 B1 | 4/2004 | Wildman et al. | |
| 6,759,959 B2 | 7/2004 | Wildman | |
| 6,825,763 B2 | 11/2004 | Ulrich et al. | |
| 7,005,968 B1 * | 2/2006 | Bridgelall | 340/10.42 |
| 7,038,584 B2 * | 5/2006 | Carter | 340/539.13 |
| 7,248,933 B2 * | 7/2007 | Wildman | 700/90 |
| 7,557,711 B2 * | 7/2009 | Volpi et al. | 340/572.1 |
| 2005/0151641 A1 | 7/2005 | Ulrich et al. | |
| 2006/0033609 A1 * | 2/2006 | Bridgelall | 340/10.42 |
| 2007/0247316 A1 * | 10/2007 | Wildman et al. | 340/572.4 |

\* cited by examiner

COMBINED LOCATING, TRACKING AND COMMUNICATIONS SYSTEM

This application is the U.S. national phase under 35 U.S.C. §371 of PCT International Application No. PCT/US2004/015107, which has an international filing date of May 14, 2004, designating the United States of America, and claims the benefit of U.S. Provisional Patent Application No. 60/470,406, which was filed May 14, 2003. The disclosures of each of these prior applications are hereby incorporated by reference herein.

CROSS-REFERENCE TO RELATED APPLICATIONS

This application claims priority of U.S. Provisional Patent Application Ser. No. 60/470,406, filed May 14, 2003, the disclosure of which is hereby expressly incorporated herein by reference.

FIELD OF THE INVENTION

The present invention generally relates to locating, tracking and communications systems, and more particularly to a combined system that provides various levels of locating and tracking resolution with communications functions.

BACKGROUND AND SUMMARY OF THE INVENTION

Caregivers such as physicians, nurses and other staff in a hospital ward, hospital wing, or other healthcare facility generally work under high pressure, high stress and long hours. These caregivers should be highly responsive to patient needs, in non-emergency as well as emergency situations. Due to ever-increasing costs of healthcare and other economic practicalities, efficient deployment of the caregivers in a healthcare facility is desired, particularly at night when the number of caregivers is typically maintained at a minimum. Nevertheless, optimizing efficiency is of secondary importance relative to the primary objective of providing a high level of healthcare. Accordingly, it is desirable to increase the efficiency of caregivers and improve the healthcare provided to patients.

The present invention provides a combined locating, tracking and communication system for a healthcare facility. The system permits wireless communication among personnel, automatically collects information relating to the location and movement of people, equipment and other items (hereinafter collectively referred to as "assets"), and provides continuously updated information describing the location and movement of such assets at varying levels of precision.

Additional features and advantages of the present invention will be evident from the following description of the drawings and exemplary embodiments.

DETAILED DESCRIPTION OF EMBODIMENTS OF THE INVENTION

Figure 1:
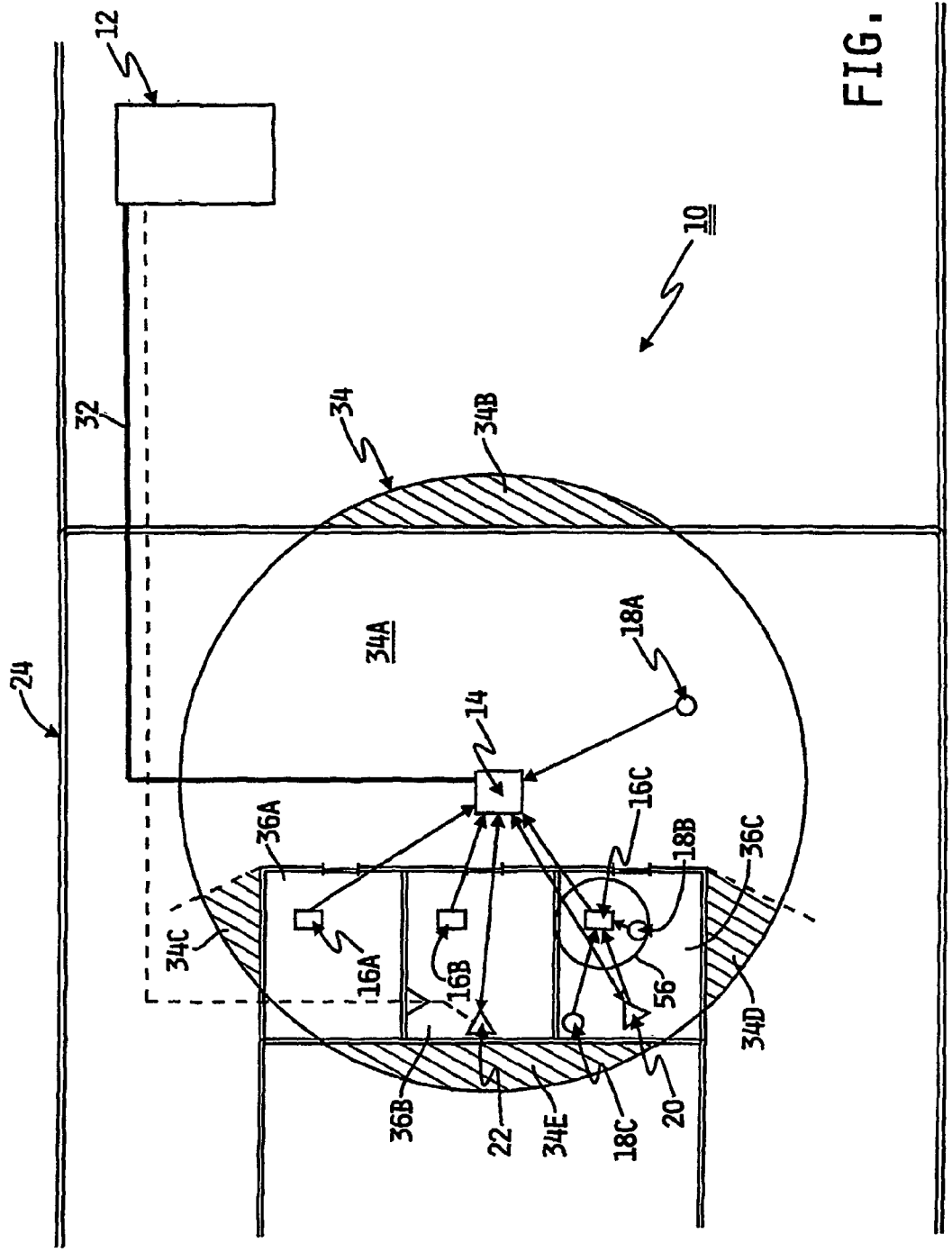
FIG. 1 is a conceptual block diagram of a system according to the present invention.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIG. 1, a combined locating, tracking and communications system 10 according to the present invention generally includes a server 12, a plurality of area transceivers 14 (only one shown) in communication with server 12, a plurality of zone transceivers 16A-C in communication with each area transceiver 14, a plurality of badges or tags 18A-C, a plurality of portable communicators 20 (only one shown), and a plurality of fixed communicators 22 (only one shown). In general, it should be understood that server 12, while shown as a single block in FIG. 1, may include multiple devices with distributed functionality. As is further described below, server 12 may facilitate operation of system 10 throughout an entire facility 24 (such as a hospital) or even multiple facilities 24. On the other hand, multiple servers 12 may be employed consistent with the following description to facilitate operation of system 10 throughout a facility 24 or throughout only a portion of a facility 24.

Figure 2:
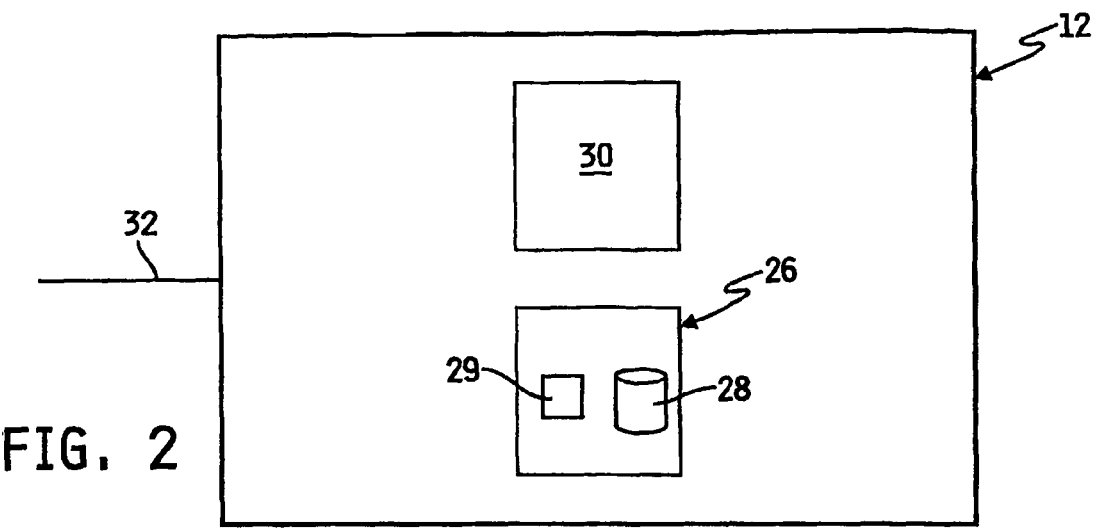
FIG. 2 is a conceptual block diagram of a server of the system of FIG. 1.

Referring to FIGS. 1 and 2, server 12 may include a computer such as a mainframe, workstation, personal computer or similar computing device capable of performing the functions described herein. As such, server 12 includes, among other things, a memory 26 having a database 28 for storing information relating to system 10 and application software 29 for execution by a processor 30, thereby facilitating the operation of system 10. Database 28 includes information that associates each portable communicator 20 with a person and each tag 18A-C with a piece of equipment, a person, or another item (hereinafter collectively referred to as "an asset"). Server 12 may be a server already present in facility 24 and used for controlling other systems such as a conventional locating and tracking system, a nurse call system, and/or a conventional communications system. Additionally, it should be understood that various features of other systems for locating and tracking assets and to support various other features of the present invention are disclosed in U.S. Pat. No. 5,561,412, U.S. Pat. No. 6,344,794, co-pending U.S. patent application Ser. No. 09/751,241, entitled "PERSONNEL AND ASSET TRACKING METHOD AND APPARATUS," filed Dec. 29, 2000, and co-pending U.S. patent application Ser. No. 09/699,796, entitled "HYGIENE MONITORING SYSTEM," filed Oct. 30, 2000, the disclosures of which are hereby incorporated by reference. Additional location and tracking systems are disclosed in U.S. Pat. Nos. 4,275,385; 4,601,064; Re 35,035; 5,633,742; 5,745,272; 5,818,617; 5,119,104; 5,387,993; 5,548,637; 5,572,195; 5,291,399; 5,455,851; 5,465,082; 5,515,426; 5,594,786; 5,689,229; 5,822,418; 5,822,544; 5,699,038 and 5,838,223.

Server 12 is connected via network 32 to the plurality of area transceivers 14, each of which provides locating, tracking and communications functions for an area 34 of a particular ward, floor, section, etc. of facility 24. To simplify this description, only one area transceiver 14 is described. Network 32 may be any of a variety of different types of networks including a LAN, WAN, or other wired or wireless network suitable for providing information transfer between server 12 and area transceivers 14 as described below. In one embodiment of the invention, network 12 is a hard-wired Ether Net that employs a conventional TCP/IP protocol. In FIG. 1, area 34, which is defined as a reception range of associated area transceiver 14, covers, among other things, a plurality of patient rooms 36A-C.

Figure 3:
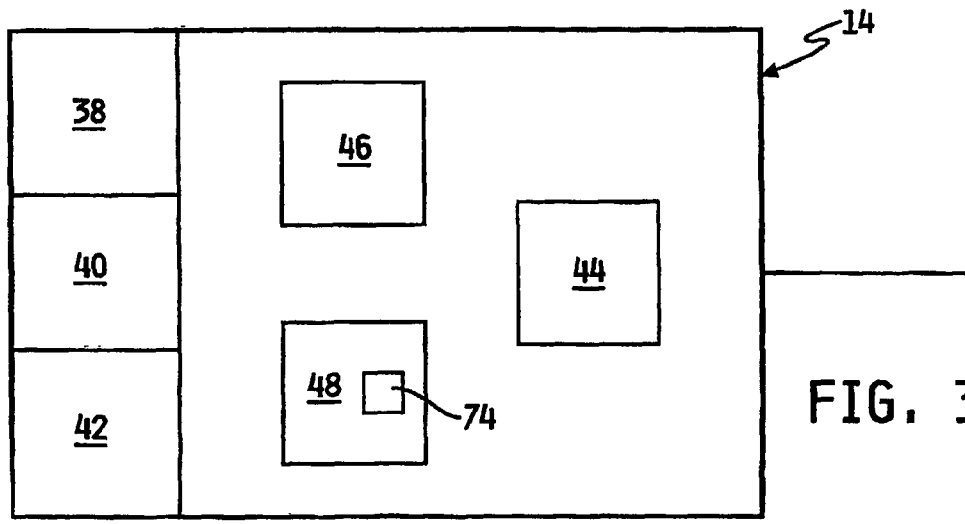
FIG. 3 is a conceptual block diagram of an area transceiver of the system of FIG. 1.

As best shown in FIG. 3, area transceiver 14 includes an IR receiver 38, an RF receiver 40, a high-frequency RF transceiver 42, a transmitter 44 connected to network 32 for communications with server 12, a processor 46, and a memory 48. Power may be supplied to transceiver 14 via a power cable (not shown) connected to a power supply available in facility 24. It should be understood that receivers 38, 40, and transceiver 42 may share certain components (e.g., antenna, electronics, etc.) or otherwise be implemented with overlapping functionality. In one embodiment, IR receiver 38 is configured to receive IR signals at multiple different IR frequencies. As is further described below, these IR signals include information that identifies a transmitting tag 18A-C, portable communicator 20, or fixed communicator 22 (hereinafter collectively referred to as "a transmitting device"). RF receiver 40 is configured to receive RF signals at multiple different RF frequencies. For example, RF receiver 40 may be configured to receive RF signals within the frequency band of 400 MHz to 900 MHz to facilitate locating and tracking at different levels of resolution as is further described below. These RF signals may also include information that identifies the transmitting device. High-frequency RF transceiver 42 is configured to receive and transmit RF signals at other RF frequencies. In this embodiment, high-frequency RF transceiver 42 is configured to receive and transmit RF signals at around 2.4 GHz (hereinafter, "high-frequency") to facilitate voice-over IP communications as well as another level of resolution of locating and tracking as is further described below.

Figure 4:
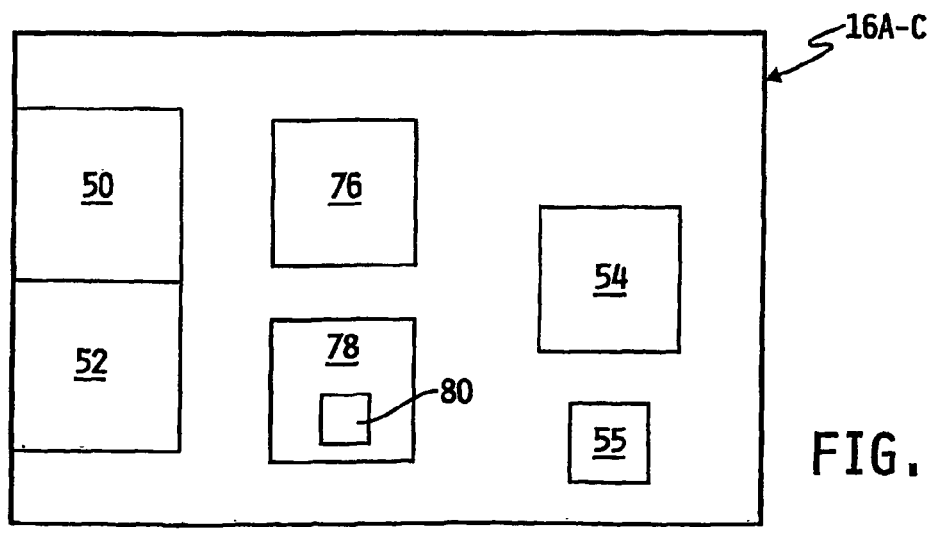
FIG. 4 is a conceptual block diagram of a zone transceiver of the system of FIG. 1.

As best shown in FIG. 4, each zone transceiver 16A-C includes an IR receiver 50, an RF receiver 52, and an RF transmitter 54 for wirelessly transmitting information relating to tags 18A-C and portable communicators 20 as is further described below. It is well within the ability of the skilled artisan to combine IR receiver 50 and RF receiver 52, or otherwise configure the receivers to share certain components. Zone transceivers 16A-C may be powered via a conventional AC outlet if available in its corresponding room 36A-C or other mounting location. Alternatively, zone transceivers may be powered by a battery 55, thereby eliminating the need to connect any wires to zone transceivers 16A-C. RF transmitter 54 is capable of transmitting information to area transceiver 14 at, for example, 900 MHz (hereinafter, "mid-frequency").

It should be understood that IR receiver 50 may receive IR signals from tags 18A-C or portable communicators 20 from any line-of-sight location within the zone of the respective zone transceiver 16A-C. For example, zone transceiver 16C may receive IR signals from any tag, such as tag 18B or 18C, or any portable communicator, such as portable communicator 20 located within room 36C, and in a line-of-sight with zone transceiver 16C. RF receiver 52, on the other hand, may receive RF signals from any tag or portable communicator within the reception range 56 of RF receiver 52. RF receiver 52 is configured such that reception range 56 is a relatively small area (e.g., two or three feet in diameter) to provide very high resolution locating and tracking information as is further described below. Thus, RF receiver 52 may be configured to receive relatively low frequency RF signals, such as 400 MHz (hereinafter, "low-frequency"), from tags 18A-C or portable communicators 20. Moreover, it should be understood that by employing known techniques, reception range 56 may be variable such that the resolution of the corresponding locating and tracking information gathered by zone transceivers 16A-C may be increased or decreased.

Tags 18A-C may be provided in a variety of different configurations, each of which is capable of transmitting an ID signal containing information that uniquely identifies the tag. For example, tags 18A-C may include features of badges for use with a locating and tracking system such as the COMposer® communications system or COMLinx™ system available from Hill-Rom® of Batesville, Ind. some details of which are disclosed in U.S. Pat. Nos. 5,561,412; 5,699,038; and 5,838,223; all of which are incorporated herein by reference, Moreover, in addition to the features described below, tags 18A-C (as well as area transceivers 14 and zone transceivers 16A-C) may incorporate RFID technology in the manner described in co-pending U.S. patent application Ser. No. 10/154,644, entitled "A WASTE SEGREGATION COMPLIANCE SYSTEM," the disclosure of which is hereby expressly incorporated herein by reference.

Figure 5:
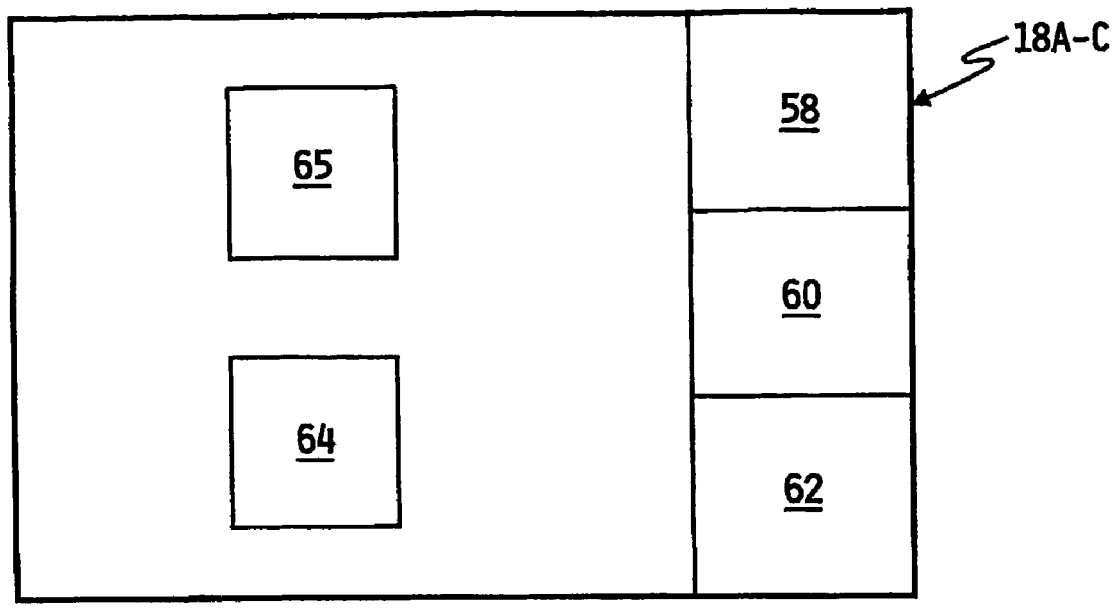
FIG. 5 is a conceptual block diagram of a tag of the system of FIG. 1.

As shown in FIG. 5, tags 18A-C may include an IR transmitter 58, a first RF transmitter 60, a second RF transmitter 62, and a power source 64 (such as a battery). Tags 18A-C may further include electronics 65 that cause the tag to periodically transmit its ID signal, to transmit its ID signal at intervals corresponding to the speed of movement of the tag, and/or to transmit its ID signal only after receipt of an excitation signal from an area transceiver 14 or a zone transceiver 16A-C as is further described below. IR transmitter 58 may be a conventional IR transmitter of the type described in U.S. Pat. No. 6,344,794 and co-pending U.S. patent application Ser. No. 09/474,357, entitled "ACTIVE BADGE OR TAG FOR A LOCATING AND TRACKING SYSTEM,"the disclosures of which are hereby expressly incorporated herein by reference. IR transmitter 58 transmits the ID signal as a line-of-sight IR signal. First RF transmitter 60 may be an RF transmitter similar to RF transmitter 54 (described above with reference to zone transmitters 16A-C). Thus, first RF transmitter 60 may, in one embodiment, transmit the ID signal as a mid-frequency RF signal having a frequency of approximately 900 MHz. Second RF transmitter 62 may be an RF transmitter configured to transmit the ID signal at a low-frequency of approximately 400 MHz.

Personal communicator 20 may be any communication device capable of wireless voice transmission and reception such as, for example, 802.11 VOIP communicators provided by Vocera. Additionally, the various different client devices described in co-pending U.S. provisional patent application Ser. No. 60/414,057, entitled "UNIVERSAL COMMUNICATIONS, MONITORING, TRACKING, AND CONTROL SYSTEM FOR HEALTHCARE FACILITY," (the disclosure of which is hereby expressly incorporated herein by reference) may be used or adapted to serve as personal communicators 20. Other conventional communication devices may include voice-enabled computing devices such as PDAs, palm-top computers, tablets, etc. In system 10, personal communicators 20 include conventional communication electronics 67 (e.g., speaker, microphone, input device, display, transmitter, etc., none shown) for providing two-way communication between multiple portable communicators 20 at a high-frequency via high-frequency transceiver 66. These voice communications signals are transmitted to transceiver 42 of area transceiver 14, which may in turn transmit the information to server 12 via network 32 and/or to another area transceiver 14 via transceiver 42. In this manner, voice communications may be facilitated between a portable communicator 20 located in area 34 and another portable communicator 20 located outside area 34.

Figure 6:
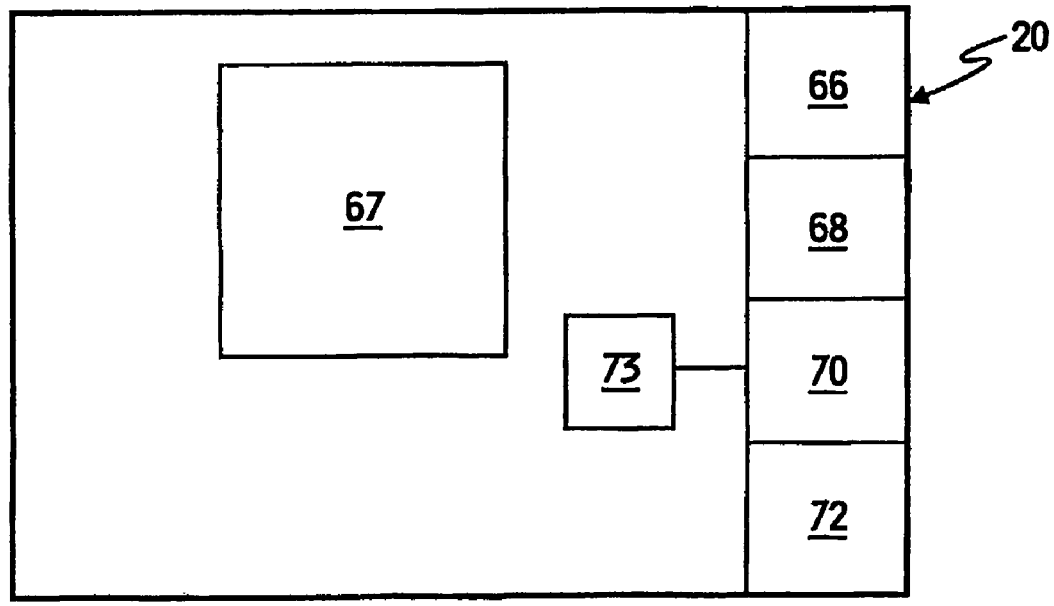
FIG. 6 is a conceptual block diagram of a portable communicator of the system of FIG. 1.

As shown in FIG. 6, in addition to communication electronics 67 and high-frequency RF transceiver 66, personal communicator 20 may include an IR transmitter 68, a first RF transmitter 70, and a second RF transmitter 72, which are substantially the same as IR transmitter 58, first RF transmitter 60, and second RF transmitter 62 of tags 18A-C, respectively. As such, portable communicator 20 may be configured to function both as a portable communicator and a tag, thereby eliminating the need for a person assigned to portable communicator 20 to also carry (or wear) a tag 18A-C.

The above-described high-frequency communication between portable communicator 20 and area transceiver 14 illustrates a first (and lowest) level of locating and tracking resolution provided by system 10. More particularly, when portable communicator 20 sends a communication signal via high-frequency RF transceiver 66 to another portable communicator 20 (inside or outside area 34), the communication signal is first received by transceiver 42 of area transceiver 14, and then forwarded to either another area transceiver 14 (if the target portable communicator 20 is outside area 34) or the target portable communicator 20 (if the target portable communicator 20 is inside area 34). Such communication signals include, in addition to voice content, information that uniquely identifies the transmitting portable communicator 20. When area transceiver 14 receives a communication signal, it forwards the identification information to server 12 via network 32, along with information identifying the receiving area transceiver 14. Processor 30 of server 12 then accesses database 28 to determine the person (e.g., nurse A) assigned to portable communicator 20 and the physical area (e.g., area 34) covered by the receiving area transceiver 14. As such, in the process of facilitating voice communications between the transmitting portable communicator 20 and the target portable communicator 20, system 10 may determine that nurse A (associated with the transmitting portable communicator 20) is located within area 34 (the area covered by the receiving area transceiver 14). Database 28 may then be updated to reflect area 34 as the last known location of nurse A.

In one embodiment of system 10, the first level of locating and tracking resolution described above may also be provided by RF transmission of ID signals from tags 18A-C or portable communicator 20. For example, as tag 18A moves within area 34, tag 18A transmits identification information as a mid-frequency RF ID signal via first RF transmitter 60, either periodically or in response to receipt of an excitation signal. This ID signal may be received by RF receiver 40 of area transceiver 14 from anywhere within area 34. When area transceiver 14 receives the ID signal, it transmits a location signal over network 32 to server 12. The location signal includes information that identifies tag 18A and area transceiver 14. Thus, processor 30 of server 12 may access database 28 to identify the asset corresponding to tag 18A and to determine the present location (i.e., area 34) of the asset based on the known location of area transceiver 14. Of course, if portable communicator 20 is configured to include RF transmitter 70 similar to RF transmitter 60 of tags 18A-C, then as the person associated with portable communicator 20 moves within area 34, RF transmitter 70 transmits a mid-frequency RF ID signal which may be processed as described above, regardless of whether the person uses portable communicator 20 for voice communications.

Another level of locating and tracking resolution provided by system 10 corresponds to IR identification signals. More specifically, system 10 is configured to determine a more specific location for assets based upon receipt of IR ID signals transmitted by either tags 18A-C or portable communicators 20. In one example, IR transmitter 58 of tag 18A transmits an IR ID signal while in area 34. This signal is received by IR receiver 38 of area transceiver 14, which in turn transmits a location signal via network 32 to server 12. The location signal includes information identifying tag 18A and area transceiver 14, and further indicating that the ID signal received from tag 18A was an IR signal. Based on this information, processor 30 of server 12 may access database 28 to identify the asset corresponding to tag 18A, and to determine that the asset must be located within area 34 (i.e., the area associated with area transceiver 14). Since the ID signal from tag 18A was an IR signal, which can only be received from locations within area 34 that are within a line-of-sight of area transceiver 14, processor 30 may further determine that the asset associated with tag 18A is located within area 34A of area 34 (areas 34B-E and rooms 36A-C are not within a line-of-sight of area transceiver 14). Of course, a portable communicator 20 equipped with IR transmitter 68 could provide the same, higher resolution locating and tracking information.

Another example of higher resolution locating and tracking based on reception of IR ID signals is room-level locating and tracking. Referring to FIG. 1, tag 18C transmits an IR ID signal to zone transceiver 16C. IR receiver 50 of zone transceiver 16C receives the IR ID signal, and transmits via transmitter 54 a mid-frequency RF location signal to RF receiver 40 of area transceiver 14. The location signal identifies tag 18C, identifies zone transceiver 16C, and indicates that the ID signal from tag 18C was an IR signal. Area transceiver 14 forwards this information via network 32 to server 12. Processor 30 of server 12 accesses database 28 to identify the asset associated with tag 18C, and to determine the area (room 36C) associated with zone transceiver 16C. Since the ID signal received from tag 18C was an IR signal, processor 30 can accurately conclude that tag 18C (and the asset associated with tag 18C) is located somewhere within room 36C. Processor 30 then updates database 28 to indicate this last known location of the asset associated with tag 18C. Additionally, if portable communicator 20 is equipped with IR transmitter 68 as described above, the IR ID signal transmitted by portable communicator 20 is received by zone transceiver 16C. This ID signal is processed in the manner described above to locate the person associated with portable communicator 20 within room 36C.

A further, still higher level of locating and tracking resolution is provided by processing low frequency RF ID signals transmitted from tags 18A-C and/or portable communicators 20. As an example of this level of resolution, zone transceiver 16C is depicted in FIG. 1 as having reception range 56. As described above, reception range 56 may cover a relatively small area, which may be variable. In one example, reception range 56 covers a three foot diameter space centered at the head of a patients bed. In this example, when tag 18B enters reception range 56 and transmits a low-frequency RF ID signal via second RF transmitter 62, RF receiver 52 of zone transceiver 16C receives the ID signal. Transmitter 54 of zone transceiver 16C then transmits a mid-frequency location signal to area transceiver 14, including information identifying tag 18B and zone transceiver 16C, and information indicating that the ID signal received from tag 18B was a low-frequency RF ID signal. Area transceiver 14 then transmits a location signal via network 32 to server 12 including this information.

Processor 30 of server 12 accesses database 28 to determine, based on the ID signal from tag 18B, the asset associated with tag 18B, and to determine that the asset is located adjacent the head of the patient bed in room 36C based on the fact that the location signal was transmitted by zone transceiver 16C and indicated that the ID signal from tag 18B was a low-frequency RF ID signal (i.e., a signal that could only be received by zone transceiver 16C if tag 18B were within reception range 56).

It should be understood that RF receiver 40 of area transceiver 14 may also receive the above-described low-frequency RF ID signals. In such an embodiment, the location of, for example, tag 18A within portion 34A of area 34 could be further resolved to a relatively small diameter reception range centered about area transceiver 14.

In summary, by configuring area transceivers 14, zone transceivers 16A-C, tags 18A-C, and portable communicators 20 with the appropriate IR and RF receivers and transmitters, server 12 can use location information from area transceiver 14 to determine that a tag 18A-C or portable communicator 20 is located (1) within area 34 based on receipt of a high-frequency RF ID signal from a portable communicator 20 or a mid-frequency RF ID signal from a portable communicator 20 or a tag 18A-C, (2) within a portion of area 34 (such as portion 34A) based on receipt of an IR ID signal from a portable communicator 20 or a tag 18A-C, (3) within a location of area 34 having a zone transceiver 16A-C (such as rooms 36A-C) based on receipt of a mid-frequency signal from a zone transceiver 16A-C indicating receipt by the zone transceiver of an IR ID signal from a portable communicator 20 or a tag 18A-C, (4) within a relatively small reception range 56 of a zone transceiver 16A-C based on receipt of a mid-frequency RF signal from a zone transceiver 16A-C indicating receipt of a low-frequency RF ID signal from a portable communicator 20 or a tag 18A-C, or (5) within a relatively small reception range 56 of an area transceiver 14 based on receipt by the area transceiver 14 of a low-frequency RF ID signal from a portable communicator 20 or a tag 18A-C.

Fixed communicators 22 may be configured such that they are substantially identical to portable communicators 20. Fixed communicators 22 are, however, mounted at fixed locations within facility 24 to serve as communication devices for individuals who may not have portable communicators 20. When an individual uses, for example, fixed communicator 22 to establish voice communications with another individual, the voice information (as well as information identifying fixed communicator 22 and information identifying the individual, is either entered by the individual into fixed communicator 22 or read by fixed communicator 22 from a tag 18A-C associated with the individual) is transmitted as a high frequency RF signal to area transceiver 14. Area transceiver 14 makes an appropriate communication connection to a target portable communicator 20 (if located within area 34) or another area transceiver 14 (if the target portable communicator 20 is located outside of area 34) in the manner described above. Additionally, information identifying the individual and the fixed communicator 22 is transmitted via network 32 to server 12. Thus, server 12 may determine that the individual is located, in this example, in room 36B (the known location of fixed communicator 22) according to the principles described above.

It should be understood that fixed communicator 22 may alternatively be connected to a movable object such as a patient bed. In such an embodiment, voice communications from and to the patient associated with the bed are not lost as the bed is moved from one location to another location. The location of the fixed communicator 22 may be determined from transmitted voice communication signals, and/or IR or RF ID signals in the manner described above.

In other embodiments of system 10, area transceivers 14 include electronics configured to perform certain aspects of the processing of ID signals to facilitate locating and tracking the transmitting devices. In this embodiment, memory 48 of area transceivers 14 store processing rules 74. For example, if area transceiver 14 receives both a high-frequency RF ID signal and an IR ID signal from a tag 18A, processor 46 may access memory 48 to determine a rule 74 associated with processing such substantially simultaneously received signals. In this instance, rule 74 may require that area transceiver 14 transmit a location signal to server 12 that indicates receipt of an IR ID signal from tag 18A, not receipt of a high-frequency RF ID signal. Rule 74 thus enables area transceiver 14 to report receipt of an ID signal that will permit a determination by server 12 of the highest resolution locating and tracking information relating to tag 18A. More particularly, receipt of a high-frequency RF ID signal from tag 18A would locate tag 18A within area 34 according to the principles described above, while receipt of a line-of-sight IR ID signal from tag 18A would more precisely locate tag 18A within portion 34A of area 34. Of course, area transceiver 14 may instead transmit a location signal to server 12 that indicates receipt of both a high-frequency RF ID signal and an IR ID signal. In such an embodiment, memory 26 of server 12 would contain the rules for processing the ID signals as described above.

Similarly, zone transceivers 16A-C (FIG. 4) may include electronics configured to perform certain aspects of the processing of ID signals to facilitate locating and tracking. For example, zone transceiver 16C may include a processor 76 and a memory 78 for storing processing rules 80. If, for example, zone transceiver 16C receives both an IR ID signal from tag 18B and a low-frequency RF ID signal from tag 18B, then processor 76 of zone transceiver 16C may access a processing rule 80 in memory 78 that requires zone transceiver 16C to report receipt of the low-frequency RF ID signal, not the IR ID signal, to area transceiver 14. The basis for rule 80 may be that the low-frequency RF ID signal more precisely locates tag 18B (i.e., to within reception range 56) than does the IR ID signal (i.e., indicating that tag 18B is located somewhere within room 36C).

It should be understood that in any of the above-described embodiments, location signals transmitted from zone transceivers 16A-C through area transceivers 14 to server 12, or simply from area transceivers 14 directly to server 12, may include time stamping. More particularly, each zone transceiver 16A-C and each area transceiver 14 may include (or be in communication with) a clock that indicates date and time of day. Alternatively, the transmitting device may include electronics for associating a date and time with each transmitted ID signal. Each location signal transmitted to server 12 may thus include time stamped information that describes the precise time of receipt (or transmission) of an ID signal from a transmitting device. As such, processor 30 of server 12 may update database 28 to indicate not only the last known location of the transmitting device, but also the date and time the transmitting device was present at that location.

It should be further understood that zone transceivers 16A-C and area transceivers 14 may be configured to perform locating of transmitting devices by using triangulation, signal strength, time stamping, and various other techniques as described in co-pending U.S. provisional patent application Ser. No. 60/462,216, entitled "ARTICLE LOCATION AND TRACKING APPARATUS AND METHOD," the disclosure of which is hereby expressly incorporated herein by reference.

Additionally, as a theft prevention measure, each portable communicator 20 may include a permanent back-up battery 73 that powers RF transmitter 70. In this manner, even where the primary battery (not shown) of portable communicator 20 is fully discharged (or removed), portable communicator 20 continues to transmit an RF ID signal. Receivers (not shown in FIG. 1), similar to zone transceivers 16A-C, but excluding IR receiver 50, may be positioned at exits or other locations of facility 24 that generally would not be passed by portable communicator 20 unless portable communicator 20 was being removed from facility 24. Upon receipt of the RF ID signal from a portable communicator 20, these receivers transmit a location signal to an area transceiver 14 that identifies the portable communicator 20, as well as the receiver. This location signal is forwarded to server 12 to update the location of the person associated with portable communicator 20 in the manner described above. Moreover, the receiver may be connected to an alarm system that indicates a theft attempt using audio and/or visual alarms, by a direct communications link that alerts security for facility 24 of a possible theft attempt, or by a link to some other system for inhibiting theft of portable communicator 20. Of course, server 12 may instead be connected to such systems, thereby eliminating the wiring requirements for the exit detection receiver.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention and the attached claims are desired to be protected.

The invention claimed is:

1. A combined locating, tracking and communications system, comprising:
   a server;
   an area transceiver configured to communicate with the server, the area transceiver having an associated reception range and being configured to transmit voice communications to one of another area transceiver and the server;
   a plurality of zone transceivers configured to communicate with the area transceiver; a plurality of tags configured to communicate with the area transceiver and the plurality of zone transceivers; and
   a plurality of portable communicators configured to communicate with the area transceiver and the plurality of zone transceivers.

2. The system of claim 1, wherein the area transceiver includes an IR receiver, an RF receiver, a high-frequency RF transceiver, and a transmitter connected to a network for communications with the server.

3. The system of claim 2, wherein the area transceiver IR receiver is configured to receive IR signals transmitted by the tags and the portable communicators, each IR signal including information that identifies one of the transmitting tag and the transmitting portable communicator.

4. The system of claim 2, wherein the area transceiver RF receiver is configured to receive signals within a frequency range of 400 MHz to 900 MHz, each RF signal including information that identifies a transmitting device.

5. The system of claim 2, wherein the area transceiver high-frequency RF transceiver is configured to receive and transmit signals at a frequency of approximately 2.4 GHz to facilitate voice-over IP communications between the portable communicators.

6. The system of claim 1, wherein each of the zone transceivers includes an IR receiver, an RF receiver, and an RF transmitter for wirelessly transmitting information relating to tags and portable communicators, the zone transceiver RF transmitter is configured to transmit information to the area transceiver at a frequency of approximately 900 MHz, and the zone transceiver IR receiver is configured to receiver line-of-sight IR signals from tags and portable communicators within a zone of the zone transceiver.

7. The system of claim 6, wherein the zone transceiver RF receiver is configured to receive RF signals from tags and portable communicators within a reception range of the RF receiver.

8. The system of claim 7, wherein the RF receiver reception range is smaller than the zone of the zone transceiver.

9. The system of claim 7, wherein the RF receiver reception range is variable.

10. The system of claim 1, wherein each of the tags includes an IR transmitter, a first RF transmitter, a second RF transmitter, and a power source, each of the tags transmits a unique ID signal containing information that identifies the tag, the tag first RF transmitter transmits the ID signal as a mid-frequency signal, and the tag second RF transmitter transmits the ID signal as a low-frequency signal.

11. The system of claim 1, wherein each portable communicator is configured to wirelessly transmit and receive voice communications to the area transceiver using an 802.11 protocol.

12. The system of claim 1, wherein high frequency communications between the portable communicators and the area transceiver define a first level of locating and tracking resolution, the communications include information that uniquely identifies a transmitting portable communicator, the area transceiver forwards the identifying information to server, which accesses a database to determine a person assigned to the transmitting portable communicator and a physical area associated with the area transceiver, and the server updates the database to reflect a last location of the person.

13. The system of claim 1, wherein mid-frequency signals from the tags and the portable communicators to the area transceiver define a first level of locating and tracking resolution, the mid-frequency signals include information that uniquely identifies one of a transmitting tag and a transmitting portable communicator, the area transceiver transmits a location signal to the server in response to receipt of a mid-frequency signal, the location signal including the identifying information, and the server accesses a database to identify an asset corresponding to the one of a transmitting tag and a transmitting portable communicator, to identify a present location of the asset, and to update the database with a last known location of the asset.

14. The system of claim 13, wherein IR signals from the tags and the portable communicators to the area transceiver define a second level of locating and tracking resolution, the IR signals include information that uniquely identifies one of a transmitting tag and a transmitting portable communicator, and the area transceiver transmits a location signal that includes the identifying information to the server, which accesses a database to identify an asset corresponding to the one of a transmitting tag and a transmitting portable communicator, to identify a present location of the asset, and to update the database with a last known location of the asset.

15. The system of claim 14, wherein IR identification signals from the tags and the portable communicators to the zone transceivers define a third level of locating and tracking resolution, a zone transceiver responds to receipt of an IR identification signal by transmitting a mid-frequency RF location signal to the area transceiver, the location signal including the IR identification signal and information identifying the zone transceiver, and the area transceiver responds to receipt of the location signal by transmitting a signal to the server, which accesses a database to identify an asset corresponding to a device that transmitted the IR identification signal, to identify a present location of the asset, and to update the database with a last known location of the asset.

16. The system of claim 15, wherein low-frequency RF identification signals from the tags and the portable communicators to the zone transceivers define a fourth level of locating and tracking resolution, a zone transceiver responds to receipt of an RF identification signal by transmitting a mid-frequency RF location signal to the area transceiver, the location signal including the RF identification signal and information identifying the zone transceiver, and the area transceiver responds to receipt of the location signal by transmitting a signal to the server, which accesses a database to identify an asset corresponding to a device that transmitted the RF identification signal, to identify a present location of the asset, and to update the database with a last known location of the asset.

17. A locating, tracking and communications system, comprising:
a server;
an area transceiver;
a portable communicator; and
a tag;
the area transceiver being configured to transmit first signals to the server upon receipt of any of high-frequency RF ID signals from the portable communicator, midfrequency RF ID signals from the portable communicator, and mid-frequency RF ID signals from the tag, the first signals indicating that an asset is within a first area.

18. The system of claim 17, wherein the area transceiver is further configured to transmit second signals to the server upon receipt of any of IR ID signals from the portable communicator and IR ID signals from the tag, the second signals indicating that the asset is within a second area that is smaller than the first area.

19. The system of claim 18, further including a zone transceiver, the area transceiver being further configured to transmit third signals to the server upon receipt of mid-frequency RF signals from the zone transceiver indicating receipt by the zone transceiver of any of IR ID signals from the portable communicator and IR ID signals from the tag, the third signals indicating that the asset is within a third area that is smaller than the second area.

20. The system of claim 19, wherein the area transceiver is further configured to transmit fourth signals to the server upon receipt of mid-frequency RF signals from the zone transceiver indicating receipt by the zone transceiver of any of low-frequency RF ID signals from the portable communicator and low-frequency RF ID signals from the tag, the fourth signals indicating that the asset is within a fourth area that is smaller than the third area.

21. The system of claim 20, wherein the area transceiver is further configured to transmit fifth signals to the server upon receipt of any of low-frequency RF ID signals from the portable communicator and low-frequency RF ID signals from the tag, the fifth signals indicating that the asset is within a fifth area that is smaller than the fourth area.

22. A locating, tracking, and communications system, comprising:
a server;
an area transceiver;
a portable communicator;
a tag;
a zone transceiver; and
a processor;
the area transceiver being configured to receive ID signals from the portable communicator, transmit first signals to the server indicating that an asset is within a first area, receive signals from the zone transceiver, and transmit second signals to the server based on signals received from the zone transceiver; the processor being configured to determine which of the first and second signals to be transmitted by the area transceiver.

* * * * *